(12) United States Patent
Haverich et al.

(10) Patent No.: US 9,107,740 B2
(45) Date of Patent: Aug. 18, 2015

(54) VESSEL CONNECTOR AND KIT HAVING AN APPLICATOR FOR SURGERY

(75) Inventors: Axel Haverich, Hannover (DE); Clemens Meyer-Kobbe, Sarstedt (DE)

(73) Assignee: corlife oHG, Hannover (DE)

( * ) Notice: Subject to any disclaimer, the term of this patent is extended or adjusted under 35 U.S.C. 154(b) by 884 days.

(21) Appl. No.: 12/596,007

(22) PCT Filed: Apr. 3, 2008

(86) PCT No.: PCT/EP2008/002653
§ 371 (c)(1),
(2), (4) Date: Oct. 15, 2009

(87) PCT Pub. No.: WO2008/125225
PCT Pub. Date: Oct. 23, 2008

(65) Prior Publication Data
US 2010/0130994 A1    May 27, 2010

(30) Foreign Application Priority Data

Apr. 16, 2007 (EP) .................................... 07007677

(51) Int. Cl.
*A61B 17/08* (2006.01)
*A61F 2/06* (2013.01)
(Continued)

(52) U.S. Cl.
CPC ................ *A61F 2/064* (2013.01); *A61B 17/11* (2013.01); *A61B 2017/1107* (2013.01); *A61B 2017/1135* (2013.01); *A61F 2/91* (2013.01); *A61F 2002/821* (2013.01)

(58) Field of Classification Search
CPC ........... A61B 17/11; A61B 2017/1107; A61B 2017/1135; A61F 2002/821; A61F 2/064; A61F 2/91

USPC ................ 606/151–153, 155; 623/1.11, 1.13, 623/1.15, 1.25, 1.28, 1.29, 1.3, 1.31
See application file for complete search history.

(56) References Cited

U.S. PATENT DOCUMENTS 3,254,651 A * 6/1966 Collito .......................... 606/153
5,316,023 A * 5/1994 Palmaz et al. .................. 606/155
(Continued)

FOREIGN PATENT DOCUMENTS

| JP | 05-161665 | 6/1993 |
| JP | 11-113937 | 4/1999 |

(Continued)

*Primary Examiner* — Julian W Woo
(74) *Attorney, Agent, or Firm* — Whitham Curtis Christofferson & Cook, PC

(57) ABSTRACT

The invention relates to a vessel connector (10) for surgically connecting two vessels and/or prosthetics to each other, comprising a sleeve-shaped body (1), the walls of which are designed to be elastic, such that the force acting on the ligature or suture is limited to the extent that no pressure points or necroses occur in the vessel. It is made of two substantially rigid outer rings (2), delimiting the sleeve-shaped body, and webs (3) present between the rings, wherein at least regions of individual webs have a shape (4) deviating from a straight line over longer distances, and it has at least one ring-shaped region (5) of higher elasticity between the rigid rings. The connector provides a blood-tight connection of at least two natural or artificial vessels, including prosthetic connections, a prosthesis to a natural vessel, or two prostheses to each other. The vessel connection is possible much faster, more easily, and more securely with the novel mechanical connector than using conventional surgical circumferential sutures.

22 Claims, 3 Drawing Sheets

(51) Int. Cl.
*A61B 17/11* (2006.01)
*A61F 2/91* (2013.01)
*A61F 2/82* (2013.01)

(56) References Cited

U.S. PATENT DOCUMENTS

| | | | | |
|---|---|---|---|---|
| 5,456,714 | A * | 10/1995 | Owen | 606/153 |
| 5,522,880 | A * | 6/1996 | Barone et al. | 606/195 |
| 5,723,003 | A * | 3/1998 | Winston et al. | 623/1.13 |
| 5,817,126 | A * | 10/1998 | Imran | 623/1.15 |
| 5,855,600 | A * | 1/1999 | Alt | 623/1.15 |
| 5,997,573 | A | 12/1999 | Quijano et al. | |
| 6,190,403 | B1 * | 2/2001 | Fischell et al. | 623/1.16 |
| 6,273,911 | B1 * | 8/2001 | Cox et al. | 623/1.15 |
| 6,277,133 | B1 | 8/2001 | Kanesaka | |
| 6,293,965 | B1 | 9/2001 | Berg et al. | |
| 6,492,615 | B1 * | 12/2002 | Flanagan | 219/121.66 |
| 6,616,675 | B1 * | 9/2003 | Evard et al. | 606/153 |
| 6,669,723 | B2 * | 12/2003 | Killion et al. | 623/1.15 |
| 6,896,697 | B1 * | 5/2005 | Yip et al. | 623/1.15 |
| 6,926,724 | B1 | 8/2005 | Chu | |
| 7,192,442 | B2 * | 3/2007 | Solem et al. | 623/1.31 |
| 7,429,268 | B2 * | 9/2008 | Shanley et al. | 623/1.15 |
| 7,744,641 | B2 * | 6/2010 | Leynov et al. | 623/1.15 |
| 8,956,400 | B2 * | 2/2015 | Beach et al. | 623/1.15 |

FOREIGN PATENT DOCUMENTS

| | | |
|---|---|---|
| JP | 2001-029351 | 2/2001 |
| JP | 2001-522692 | 11/2001 |
| WO | 9925273 A1 | 5/1999 |

\* cited by examiner

VESSEL CONNECTOR AND KIT HAVING AN APPLICATOR FOR SURGERY

INTRODUCTION

The invention relates to a vessel connector for surgically connecting at least two vessels to each other, including both natural and artificial vessels and also prostheses, and to a kit for vascular surgery which is composed of such a vessel connector and of an applicator with a dome-shaped projection. The invention therefore relates generally to the field of surgical vascular connecting techniques, for example for connecting two natural vessels, for connecting a vessel to a prosthesis or to a vascular attachment piece of said prosthesis, or for connecting two prostheses to each other.

PRIOR ART

Two blood vessels are traditionally connected by a surgical suture. Various suturing techniques have been developed, such as button sutures, mattress sutures, and continuous sutures, and have later been transferred to connecting a natural blood vessel to a vascular prosthesis. At present, a continuous overlapping suture is generally used for artificially connecting a blood vessel to a vascular prosthesis. A continuous suture is also used when connecting two prostheses to each other.

The suture material is either composed of braided plastic or of what are called monofilament threads. The latter are preferred in vascular surgery, because the puncture channels which they produce are only very narrow and there is therefore hardly any further loss of blood from the puncture channels when circulation of blood through the vessel is re-established.

Depending on the intended purpose, use is made of suture materials that are not resorbable in the body, such as polyamides, polyethylene terephthalates, polypropylene types, and others, or of materials that are resorbable in the body, such as PDS (poly-p-diaxanone), lactide copolymers, polyglactin or others.

A circumferential suture, that is to say a suture around the entire circumference of the vessel, is time-consuming. On average, the surgeon has to allow between 6 and 10 minutes for this. In an arterial vascular suture, the flow of blood through the vessel has to be interrupted, with the result that the flow of blood through the tissue supplied from the artery is reduced for a time. In most anatomical situations arising in vascular surgery, this is not critical. However, there are organ systems in which the tissue has only slight tolerance to reduced circulation of blood. This applies particularly to the brain. There, and also in other major artery segments, phases of clamping off, which have to be accepted in order to produce reconstructive vascular anastomoses, can lead to a critical reduction in the circulation of blood through individual or even multiple organs.

There are also anatomical locations where not all sections of a series of vascular sutures are easily visible or accessible to conventional surgical instruments. An example of a region that is difficult to access is the left subclavian artery if, as is often necessary, the surgery has to be performed by a median sternotomy.

A classical suture can also present great difficulties if the underlying disease has caused a splitting of the vessel wall (arterial dissection). In this case, it can happen that the arterial wall, which has split into two layers, does not withstand, if it is punctured in each case alone, the pull of the needle and of the thread, resulting in tearing and subsequent bleeding from the vascular anastomosis.

As early as 1900, Payr described a vascular anastomosis method using absorbable cannulas made of magnesium. Later, other materials were discussed, such as silver or ivory. In 1958, Demichow[1] described a vessel connector means composed of collodium. Here, the tube was pulled back over one end of the vessel, the vessel being inverted with the intima to the outside and being fixed with a ligature. The second vessel was drawn over the intima of the first vessel and fixed. This method entails a risk of pressure points developing on the ligatures after about 5 days and leading to necrosis. A consequence of the necrosis is that the vascular connection comes loose.

The patent specifications U.S. Pat. No. 6,553,812, U.S. Pat. No. 6,440,163, U.S. Pat. No. 6,309,416 and U.S. Pat. No. 6,113,612 describe vessel connector means and associated application aids. The vessel connector means are rivet-shaped structures or tubular vessel connector means which fix the vessels with the aid of staples and barbs. The authors of these had heart bypass surgery particularly in mind.

German patent application DE10345986.9 of Oct. 7, 2003 describes a rigid, tubular vessel connector means that has an aperture for a suture for fixing the vessels.

Object

In light of the vessel connector structures known in the prior art, the object of the invention is to develop an aid and a method with which two vessels (including artificial vessels and prostheses) can be permanently connected quickly and in an uncomplicated way, even in areas where surgical access is difficult or even in cases where the wall vessel has been weakened, another aim at the same time being to avoid reduced blood circulation and necrosis.

To achieve this object, it is necessary for vessel connector and ligature to interact in such a way that on the one hand a stable connection is produced, while the pressure on the patient's natural co-connected tissue is nevertheless kept as low as possible.

Solution

To achieve this object, the vessel connector according to the invention for surgically connecting vessels and/or vascular prostheses by ligature on a sleeve-shaped body is characterized by two substantially rigid outer rings, which delimit the sleeve-shaped body, and by webs located between the rings, and also by at least one annular area of greater, elasticity between the rigid rings, at least some areas of individual webs having a shape of substantial length deviating from the straight line.

The measure whereby at least some areas of individual webs, viewed along the length of the sleeve, have a shape of substantial length deviating from the straight line (in particular from the direct connection between the rings) affords, in a constructive way, a greater elasticity in the radial direction in this area, as is desired for the purposes of the invention.

By virtue of the measures according to the invention, the sleeve-shaped body of the vessel connector is so configured that the force acting on vessel wall and suture or ligature is limited, such that no pressure points or necroses occur. Nevertheless, a blood-tight connection can be produced by ligature or suture.

In a preferred embodiment, the sleeve-shaped body or the tube body is substantially cylindrical. The body then has the shape of a simple cylindrical sleeve. However, this does not rule out the possibility that it may be expedient, in certain applications, if the sleeve-shaped body is arc-shaped or s-shaped.

The length of the connector means is preferably ca. 4 to 16 mm in total. The diameter of the connector means is preferably between 4 mm and 30 mm.

For the ligature, monofilament suture material can be used, but it is preferable to use multifilament material, e.g. cotton umbilical tape (diameter ca. 2 mm).

The outer rings of the vessel connector are rigid, i.e. are fixed in shape or substantially rigid during normal handling and when used as intended, which is meant to signify that they are less elastic than the at least one annular area of greater elasticity provided on the connector.

The elasticity of the annular area is related to the behavior when pressure is applied in the radial direction. The area is intended to behave elastically in relation to a radially exerted pressure, i.e. is intended to yield in the direction of the center axis of the connector. This behavior should be relatively more elastic than that of the rigid outer rings.

The degree of elasticity is dependent on the surgical application and can be achieved automatically by the features according to the invention as described below in more detail with reference to the examples. The elasticity thus derives from the web design and can be adjusted with the aid thereof.

Webs are located between the outer rings. These webs can be connected to the outer rings and to other web-shaped, e.g. plate-shaped or annular areas. Preferably, however, the outer rings are connected to webs extending from one ring to the other ring.

According to one embodiment of the invention, the annular area of greater elasticity is located in the center of the vessel connector, or several annular areas are arranged symmetrically with respect to the center.

For the annular areas of greater elasticity, it is preferable that all webs extending through same have extended lengths within the area.

The shape of substantial length deviating from the straight line is achieved by designing the webs such that the individual web between two points A and B describes a path that is longer than the direct, straight, i.e. shortest connection between A and B. In a preferred embodiment, this is afforded by an s-shaped, z-shaped, wave-shaped or meandering web structure. The increase in the length of the webs compared to the straight line should be at least 10%.

The webs can be unbranched, branched, or at least in some areas interlinked or, as in a woven fabric or knit, interlaced.

In a particularly preferred illustrative embodiment of the invention, two annular areas of an s-shaped or z-shaped or wave-shaped or meandering web structure surround a central area of substantially straight web sections, in order thereby to form an annular area of greater elasticity, such that overall an area of greater elasticity is obtained. If this vessel connector is radially annularly constricted in the area of the straight web sections, i.e. approximately at the center of the elastic area, a profile drawn in approximately in a U-shape is obtained if the pressure is sufficient. By virtue of the possibility of configuring such a profile, the suture is at the same time positioned on the sleeve-shaped body, since it is automatically located at a point of relatively smallest diameter as a result of the fixing.

Generally, therefore, in the invention, means for positioning a ligature over the connector can be formed by virtue of a central annular area of greater elasticity being surrounded by comparatively more rigid, sleeve-shaped areas adjoining the outer rings. With several elastic areas, this can also be effected multiply on a vessel connector, for example in order to offer several possible positions on a connector for the ligature, or in order to be able to connect more than two vessels or prostheses. Said means can also be provided multiply in order to position different ligatures individually, e.g. on a branched vessel connector. For this purpose, it is possible, for example, for a central annular area of relatively lower elasticity to be surrounded by two annular areas of relatively greater elasticity. A branched vessel connector can preferably be branched in a T-shape or Y-shape.

Of course, it is also possible for the sleeve-shaped body already to decrease in diameter from the edge toward the center in the relaxed position or rest position, or generally to have several positions of smaller diameter.

The wall structure of the vessel connector is generally configured such that the wall of the sleeve-shaped body is so thin in some areas, or completely broken through, such that overall an elastic structure is obtained. The desired structure can preferably be cut from a tube or can be composed of a braid of wires.

The material strength and material properties of the wall are chosen such that sufficient stability for fixing the prosthesis and/or the vessels is ensured, but such that no pressure points develop on the vessels at the ligature or suture, which pressure points may lead to necrosis.

According to a particularly preferred embodiment of the invention, the webs are cut free from the sleeve-shaped body of the vessel connector. The openworked embodiment has the advantage that the apertures thus obtained can be used to pass through needles or other surgical suturing tools for pulling a surgical suture material through.

For the ligature, the connector means is inserted into the prosthesis or into the vascular stump that is to be attached. In the case of a simple connector means with only one ligature position, the connector means, together with the prosthesis pulled over it or the vascular stump pulled over it, is fitted into the open end of the vessel that is to be attached, such that a three-layer structure results (from the inside outward: connector means, prosthesis/vessel, vessel). A thread is looped (or wound, ca. 1-3 windings) around all three layers together at the intended position and then tied by means of a surgical knot. In a connector means with at least two ligature positions, the first ligature can be prepared in advance of surgery, when a prosthesis is to be attached, by inserting one end of the connector means into the prosthesis and connecting it by ligature (as described above, but with only 2 layers, namely connector means and prosthesis). During surgery, the prepared prosthesis is inserted, with the connector means still free at one end, into the open vascular stump and connected in the same way (2 layers) by ligature. Two natural vessels are connected in a corresponding manner during surgery.

The openworked embodiment also has the advantage that a sufficient microcirculation is ensured in the suture or ligature area, and therefore a sufficient supply of blood and oxygen to the vessels beyond the suture or ligature, thereby also reducing the danger of necrosis.

In an alternative embodiment, the webs can stand in relief on a film-like thin sleeve. For this purpose, the material between the webs is removed in films, for example using a laser. At least in the area of the fixing or ligature, up to 50 to 80% of the surface of the vessel connector is broken through or removed.

The vessel connector can be made from all mechanically suitable materials that are approved, and have sufficient strength, for use in the human or animal body. Many such materials, which are also used for example for orthopedic and dental implants, surgical instruments, heart valves and the like, are familiar to a person skilled in the art in the field of surgery and implantology.

In a preferred embodiment, the vessel connector is made of metal, preferably titanium, a titanium alloy or stainless steel.

Generally, the following materials can be used: metals, in particular titanium or stainless steel, including the special alloys used for implants and medical instruments, carbon materials, including carbon fiber meshes, soft plastic, for example silicone, hard plastic, for example TEFLON, ceramic material and bioresorbable material.

According to one possible embodiment, the tubular or sleeve-shaped body of the vessel connector can have a substantially cylindrical middle part made of a relatively harder material and smooth or trumpet-shaped attachments made of a relatively softer material. The ligature or suture is then applied in the area of the harder material, while the widened or only softer ends of the vessel connector permit modeling to the vessel wall/prosthesis wall.

The vessel connector according to the invention can be provided entirely or partially with a coating and/or structure that prevents or at least reduces the adherence of blood constituents, preferably entirely or partially on the inner face, i.e. luminal face.

Such a coating can be composed of a material that smoothes the surface or increases the slidability on the surface. For a coating that increases slidability, it is possible, for example, to use a polybutylate or a mixture or a copolymer with polybutylate. The coating could also contain antithrombotic medicaments, e.g. heparin. It is also possible to provide a coating that generates a lotus effect on the surface. The lotus structure can alternatively also be formed directly on the surface of the sleeve-shaped body, without separate coating. Coated and structured surfaces for medical devices are known, for example, from WO 00/07633 or from DE 199 50 452.

In a development of the invention, the vessel connector comprises, at least on one of the outer rings, a collar-shaped projection acting as an abutment for a dome-shaped applicator to be inserted into the vessel connector.

The invention further comprises a kit composed of a vessel connector and of an applicator with a dome-shaped projection for surgically connecting vessels and/or vascular prostheses, preferably by ligature. The vessel connector is mounted on the dome-shaped projection and brought into position with the latter, as is described in more detail with reference to the figures. The dome serves on the one hand as a limiting means, to ensure that the ligature is not tied too tightly, and on the other hand positions the connector means at the right location.

The invention is explained in more detail below with reference to examples shown in the drawing. The examples have been chosen for illustrative purposes and are not intended to limit the general possibilities of the invention. In the drawing.

Figure 1:
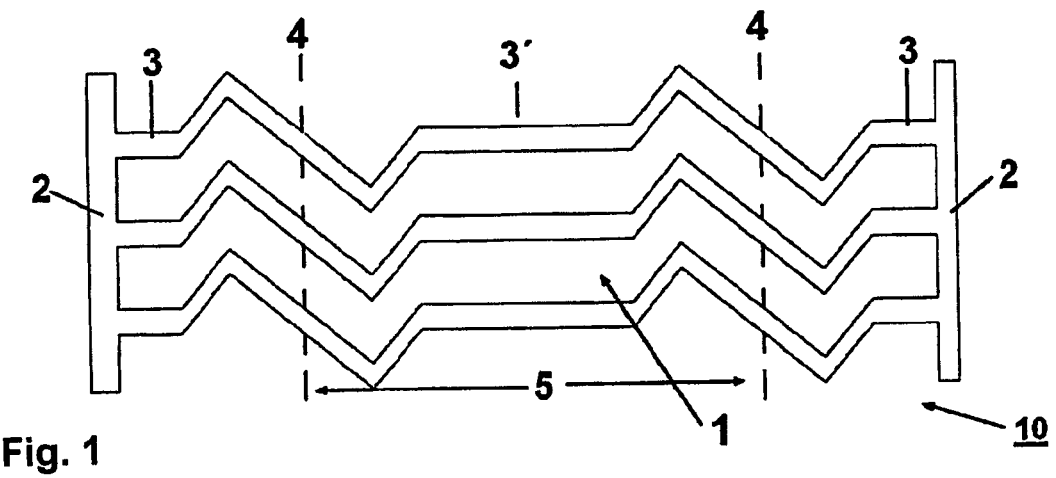
FIG. 1 shows a side view of a first illustrative embodiment of a vessel connector.

FIG. 1 shows a first illustrative embodiment of a vessel connector designated overall by 10 and composed of a sleeve-shaped body 1 which is delimited at its edges by two substantially rigid rings 2. The rings 2 are connected by webs 3 that run from one ring to the other. Along two annular areas, here arranged symmetrically with respect to the center, the webs 3 have waves 4 which each form shapes of substantial length deviating from the straight line (and each generally designated by 4). By stretching these wave-shaped structures, an easily adjustable elasticity is achieved by constructional means. In this way, in this vessel connector 10, an annular area 5 of overall greater elasticity extends across both wave-shaped areas and the straight web sections 3' which lie therebetween and on which the ligature can be positioned.

Figures 2A, 2B, 2C, 2D:
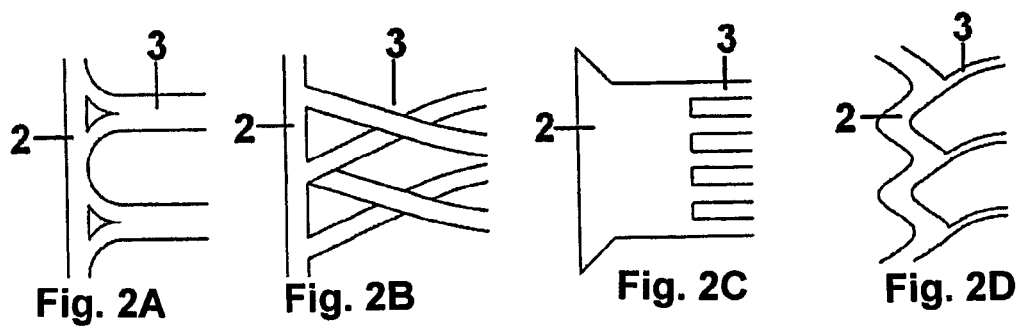
FIG. 2 shows details of the attachment of web structures to an outer ring.

FIG. 2 shows various possible structures for the edge areas of a vessel connector 10 at the transition between ring 2 and webs 3. These edge areas are each intended to be stiffer than at least one annular elastic area 5 lying between the rings, although they themselves can have a certain degree of inherent elasticity.

Figures 3A, 3B, 3C, 3D:
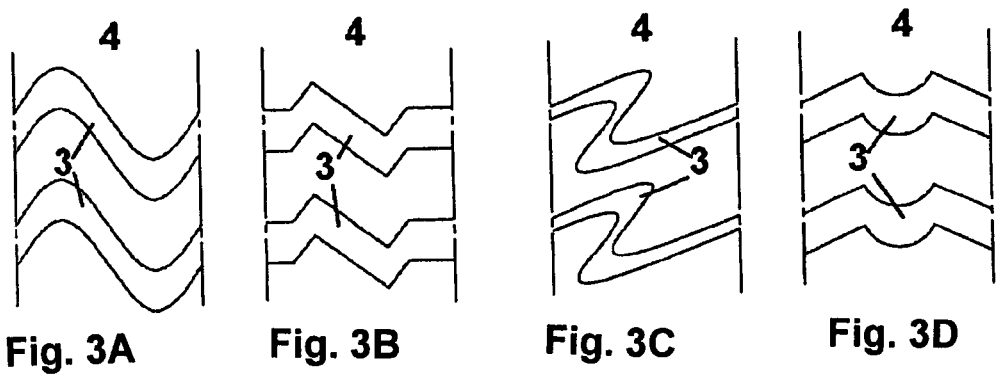
FIG. 3 shows details of structures providing an increase in length.

FIG. 3 shows various possible structures for the shapes 4 of substantial length deviating from the straight line within the webs 3. By stretching of these structures or shapes 4 upon loading, elasticity is made available in constructional terms. Depending on the overall design, the annular area 5 of greater elasticity can coincide with an individual annular area of extended web lengths (various shapes 4), or the area 5 of greater elasticity is formed by two such areas of extended web lengths with a ligature zone lying therebetween (for example from straight web sections). An example of this is shown in FIG. 1.

Figure 4A:
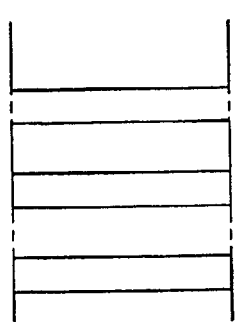
FIG. 4 shows details of central areas/suture positioning sites.
Figure 4B:
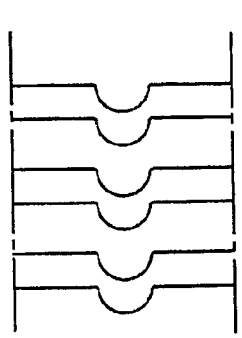
Figure 4C:
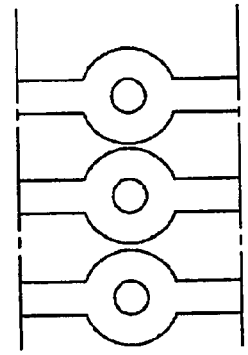

FIG. 4 shows possible structures for central areas of the sleeve-shaped bodies 1 which can lie between two areas, as shown in FIG. 3.

Figure 5:
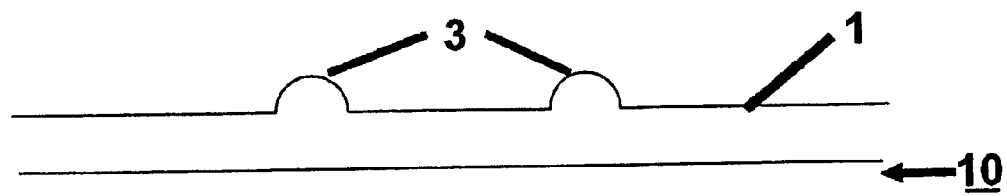
FIG. 5 shows a cross section through a wall from which some of the material has been removed in films.

FIG. 5 illustrates an alternative embodiment. It shows a cross section through the side wall of the connector 10. In this case, the webs 3 only stand in relief on a film-like thin sleeve-shaped body 1. For this purpose, the material between the webs 3 is removed, for example by a laser, until only a film-like layer of the originally uniformly thick cylindrical main body remains. The layer can be very easily bent or twisted, such that an elasticity can be obtained corresponding to that in the apertured embodiment.

Figure 6:
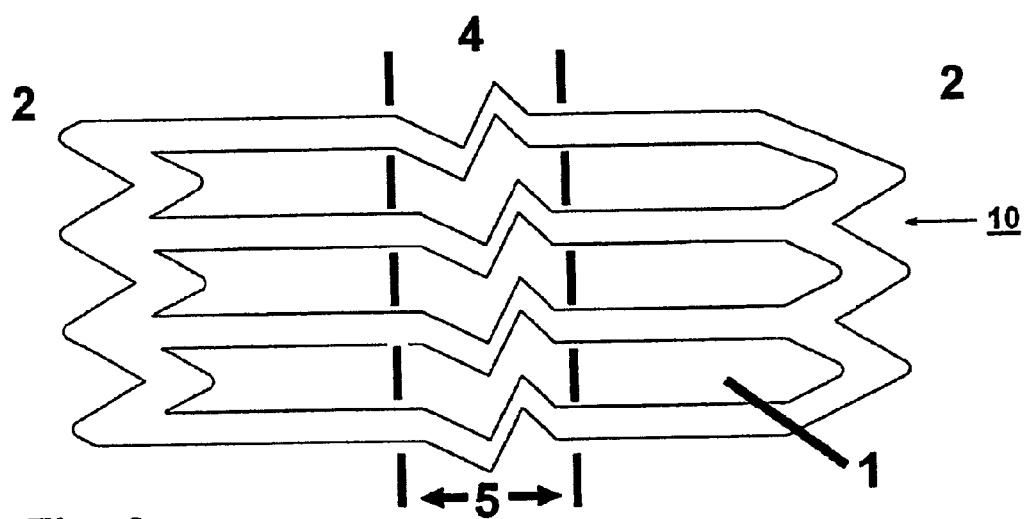
FIG. 6 shows a side view of a second illustrative embodiment of a vessel connector.

FIG. 6 shows another illustrative embodiment with serrated rings 2. This structure may possibly be recommended for better adaptation to irregular vessel shapes. Otherwise, identical reference signs designate identical structural parts.

Figure 7:
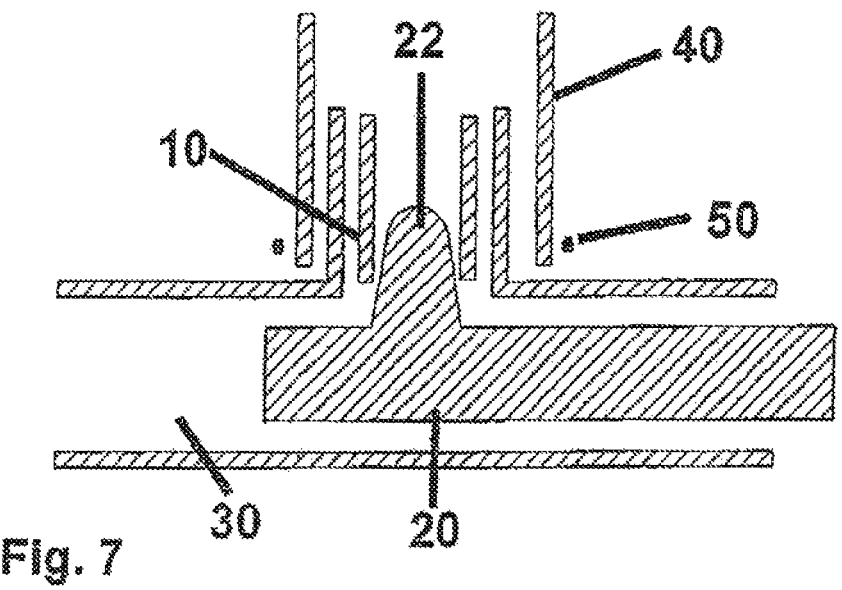
FIG. 7 shows a cross section through applicator, vessel connector, T-shaped vascular prosthesis and the vascular stump to be attached, in a situation during surgery.

FIG. 7 shows an illustrative embodiment of a vessel connector 10 inserted with an applicator 20 into a vascular prosthesis 30, in a situation during surgery. The vessel connector 10 is first placed onto a dome 22 of the applicator and guided through the prosthesis 30 to the anchoring position. A vessel 40 to be attached is pulled over the end of the prosthesis 30 with the vessel connector 10 lying under the latter. The vessel connector maintains its fixed position through the applicator 20. Finally, the vessel connector 10 is tied to the prosthesis 30 and, to the vessel 40. The ligature is indicated at 50. The dome 22 serves as a limiting means and prevents too tight a ligature, while at the same time it holds the vessel connector with a form-fit at the desired position. If appropriate, the dome can be provided with an abutment against which the vessel connector abuts upon insertion into the vessel.

Figure 8:
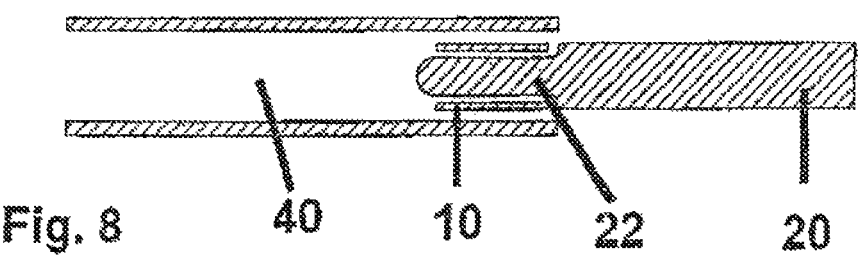
FIG. 8 shows a cross-sectional view of an alternative example of an applicator in the position of use.

FIG. 8 shows an alternative illustrative embodiment of an applicator 20, which is provided for other vessel or prosthesis geometries, in the associated position of use (outlined).

The invention claimed is:

1. A vessel connector for surgically connecting vessels or vascular prostheses by ligature, comprising
   a sleeve-shaped body having
      two spaced apart rigid outer rings being fixed in shape, and
      a plurality of webs connected to said two spaced apart rigid outer rings and which extend longitudinally between said two spaced apart rigid rings, said plurality of webs having outer sections adjoining each of the two spaced apart rigid outer rings and at least one annular area between said outer sections,
   wherein said sleeve-shaped body has a center axis which passes through said two spaced apart rigid outer rings, and
   wherein said at least one annular area is configured to yield elastically in a radial direction towards said center axis when pressure is applied, and
   wherein the at least one annular area is of greater elasticity than the outer sections and the outer sections are of greater elasticity than the two spaced apart rigid outer rings and
   wherein the at least one annular area is configured to have a smaller diameter than the outer sections and the outer sections are configured to have a smaller diameter than the two spaced apart rigid outer rings when pressure is applied to the at least one annular area.

2. The vessel connector as in claim 1, wherein each of said plurality of webs are longer in length than a straight line between said two spaced apart rigid rings.

3. The vessel connector as in claim 1, wherein said at least one annular area is centrally located between said two spaced apart rigid outer rings.

4. The vessel connector as in claim 1, wherein each of said plurality of webs have at least one section which extends along a straight line between said two spaced apart rigid outer rings and at least one deviating section which deviates from said straight line at said at least one annular area.

5. The vessel connector as in claim 4, wherein said at least one deviating section has a shape selected from the group consisting of s-shaped, z-shaped, wave shaped and meandering web structure.

6. The vessel connector as in claim 1, wherein said at least one area of said plurality of webs located between said two spaced apart rigid outer rings includes at least two annular areas both of which are configured to yield elastically in said radial direction towards said center axis when pressure is applied.

7. The vessel connector as in claim 1, wherein each of said plurality of webs is at least 10% longer than a straight line extending between said two spaced apart rigid outer rings.

8. The vessel connector of claim 1 wherein said two spaced apart rigid outer rings are the only rigid rings in said vessel connector.

9. The vessel connector of claim 1, wherein the outer sections of the plurality of webs adjoining the two spaced apart rigid outer rings comprises a plurality of axially oriented members.

10. A vessel connector for surgically connecting vessels or vascular prostheses by ligature, comprising
    a sleeve-shaped body having
       two spaced apart rigid outer rings being fixed in shape, and
       a plurality of webs connected to said two spaced apart rigid outer rings and which extend longitudinally between said two spaced apart rigid rings, said plurality of webs having outer sections adjoining each of the two spaced apart rigid outer rings and at least one annular area between said outer sections,
    wherein said sleeve-shaped body has a center axis which passes through said two spaced apart rigid outer rings, and
    wherein said at least one annular area is configured to yield elastically in a radial direction towards said center axis when pressure is applied, and
    wherein the outer sections have a greater elasticity than the at least one annular area and the at least one annular area has a greater elasticity than the two spaced apart rigid outer rings and
    wherein the outer sections are configured to have a smaller diameter than the two spaced apart rigid outer rings when pressure is applied to the at least one annular area.

11. The vessel connector as in claim 1, wherein said plurality of webs are openwork cut out from said body of said vessel connector.

12. The vessel connector as in claim 1, wherein said plurality of webs stand in relief on a film-like thin sleeve comprising said sleeve-shaped body.

13. The vessel connector as in claim 1, wherein said vessel connector is made of a substance selected from the group consisting of titanium, stainless steel, titanium alloys, stainless steel alloys, carbon, plastic, and bioresorbable material.

14. The vessel connector as in claim 13, wherein said vessel connector is made from plastic.

15. The vessel connector as in claim 13, wherein said vessel connector is made from titanium.

16. The vessel connector as in claim 1, further comprising a coating on at least one surface of said plurality of webs.

17. The vessel connector of claim 16, wherein said coating is an antithrombotic agent.

18. The vessel connector of claim 16, wherein said coating is a material that increases slidability on the surface.

19. The vessel connector as in claim 1, wherein at least one of said two spaced apart rigid outer rings has a collar-shaped projection, which provides an abutment for an applicator.

20. The vessel connector of claim 10, wherein the outer sections of the plurality of webs adjoining the two spaced apart rigid outer rings comprises a plurality of axially oriented members.

21. A kit for surgically connecting vessels or vascular prostheses, comprising
    a vessel connector comprising a sleeve-shaped body having two spaced apart rigid outer rings being fixed in shape and a plurality of webs connected to said two spaced apart rigid outer rings and which extend longitudinally between said two spaced apart rigid outer rings, said plurality of webs having outer sections adjoining each of the two spaced apart rigid outer rings and at least one annular area between said outer sections,
    wherein said sleeve-shaped body has a center axis which passes through said two spaced apart rigid outer rings, and wherein the at least one annular area is configured to yield elastically in a radial direction towards said center axis when pressure is applied in said at least one annular area, and wherein both the at least one annular area and the outer sections have greater elasticity than the two spaced apart rigid outer rings and the elasticity of the at least one annular area and the outer sections is different and wherein the at least one annular area is configured to have a smaller diameter than the outer sections and the outer sections are configured to have a smaller diameter than the two spaced apart rigid outer rings when pressure is applied to the at least one annular area, and an applicator with a dome-shaped projection on which said vessel connector can be placed for surgically connecting vessels or vascular prostheses by ligature.

22. The kit of claim 21, wherein the outer sections of the plurality of webs adjoining the two spaced apart rigid outer rings comprises a plurality of axially oriented members.

\* \* \* \* \*